United States Patent

Begrich

[11] 3,939,158
[45] Feb. 17, 1976

[54] N-(2,4-DIHALO-S-TRIAZIN-6-YL)-UREAS AND PROCESS FOR THEIR MANUFACTURE

[75] Inventor: Rainer Begrich, Basel, Switzerland

[73] Assignee: Ciba-Geigy AG, Basel, Switzerland

[22] Filed: Aug. 8, 1974

[21] Appl. No.: 495,594

[30] Foreign Application Priority Data
Aug. 17, 1973 Switzerland.................. 11870/73

[52] U.S. Cl............ 260/249.5; 252/301.2 W; 8/1 E
[51] Int. Cl.². ........................................ C07D 251/50
[58] Field of Search ................................ 260/249.5

[56] References Cited
UNITED STATES PATENTS

| | | | |
|---|---|---|---|
| 3,660,393 | 5/1972 | Ackermann et al. ............ | 260/249.5 |
| 3,849,413 | 11/1974 | Begrich et al. .................. | 260/249.5 |

FOREIGN PATENTS OR APPLICATIONS 2,263,853   7/1973   Germany

Primary Examiner—John M. Ford
Attorney, Agent, or Firm—Joseph G. Kolodny; Prabodh I. Almaula; Edward McC. Roberts

[57] ABSTRACT

A process for the manufacture of N-(2,4-dihalo-s-triazin-6-yl)-ureas of the formula

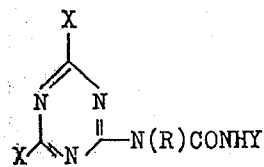

(1), wherein X represents halogen, R represents alkyl, aryl or hydrogen and Y represents hydrogen or the sulphonic acid group, which comprises reacting a dihaloamino-s-triazine of the formula

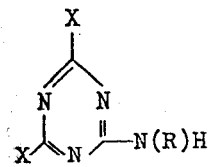

(2), wherein X and R have the meanings assigned to them hereinbefore, with chloro-sulphonylisocyanate and hydrolysing the resulting reaction product. The compounds of the formula (1) are suitable as starting products for the manufacture of reactive dyes, fluorescent whiteners or agro - chemicals.

9 Claims, No Drawings

N-(2,4-DIHALO-S-TRIAZIN-6-YL)-UREAS AND PROCESS FOR THEIR MANUFACTURE

The present invention provides a process for the manufacture of N-(2,4-dihalo-s-triazin-6-yl)-ureas of the formula

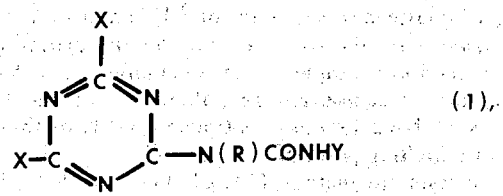

wherein X represents halogen, R represents alkyl, aryl or hydrogen and Y represents hydrogen or the sulphonic acid group.

According to the process of German Offenlegungsschrift 2 230 070, it is possible to react s-triazinylisocyanates with water-soluble primary or secondary amines or preferably with ammonia to yield N-(2,4-dihalo-s-triazin-6-yl)-ureas. The s-triazinylisocyanates used as starting materials are obtained by reaction of dihalo-amino-s-triazines with oxalic dichloride.

It has now been discovered that N-(2,4-dihalo-s-triazin-6-yl)-ureas of the formula (1) can be obtained by reacting a dihalo-amino-s-triazine of the formula

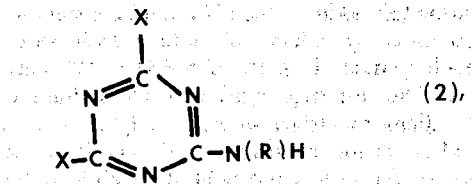

wherein X and R have the meanings assigned to them in respect of the formula (1,) with chlorosulphonylisocyanate, ClSO$_2$NCO [Angew. Chem. 80, 179–189, 1968)], and hydrolysing the resulting reaction product. The hydrolysis can be performed in acid or alkaline solution.

The acid hydrolysis yields a N-(2,4-dihalo-s-triazin-6-yl)-urea of the formula

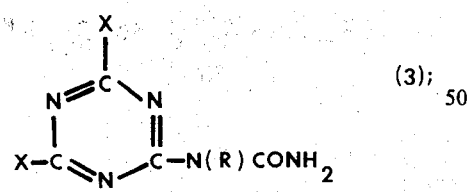

and acid is split off. Alkaline hydrolysis yields a N-(2,4-dihalo-s-triazin-6-yl)-N'-sulpho-urea of the formula

or a sulphonic acid of this compound.

Preferred starting compounds are dihalo-amino-s-triazines of the formula (2), wherein X represents chlorine and R represents alkyl with 1 to 4 carbon atoms, phenyl or hydrogen. The most important starting compound is 2,4-dichloro-6-amino-s-triazine.

The reaction of the dihalo-amino-s-triazine with the chlorosulphonylisocyanate is desirably performed in such a manner that the chlorosulphonylisocyanate is added dropwise to the solution of the dihalo-amino-s-triazine in an organic solvent and the addition is so controlled that the reaction temperature does not appreciably exceed room temperature. It is advantageous to use an organic solvent that is miscible with water, e.g. acetronitrile or dioxan, so that the hydrolysis can be carried out in the same solution without prior separation of the product formed by the reaction of the dihalo-amino-s-triazine with chlorosulphonylisocyanate. The acid hydrolysis is then effected by addition of water to the reaction solution. Alkaline hydrolysis takes place following the reaction of the chlorosulphonylisocyanate with the dihalo-amino-s-triazine in a water-miscible organic solvent by adding the reaction solution to water that contains a buffer substance. Instead of adding a buffer substance to the water it is also possible to keep the pH of the solution in a weak alkaline range by addition of a base, e.g. sodium hydroxide solution.

The above mentioned reaction product which is forming during the reaction of the dihalo-amino-s-triazine with chlorosulphonylisocyanate results from addition of chlorosulphonylisocyanate to the dihalo-amino-s-triazine and probably has the structure of a N-(2,4-dihalo-s-triazin-6-yl)-N'-(chlorosulphonyl)-urea.

Examples of dihalo-amino-s-triazines of the formula (2) are:
2,4-dichloro-6-amino-s-triazine,
2,4-dibromo-6-amino-s-triazine,
2,4-difluoro-6-amino-s-triazine,
2,4-dichloro-6-N-methylamino-s-triazine,
2,4-dibromo-6-N-ethylamino-s-triazine,
2,4-dichloro-6-N-propylamino-s-triazine,
2,4-dichloro-6-N-isopropylamino-s-triazine,
2,4-dichloro-6-N-butylamino-s-triazine,
2,4-dichloro-6-N-pentylamino-s-triazine,
2,4-dichloro-6-cyclohexylamino-s-triazine,
2,4-dichloro-6-N-phenylamino-s-triazine,
2,4-dibromo-6-N-phenylamino-s-triazine,
2,4-dichloro-6-N-(4'-methylphenyl)amino-s-triazine,
2,4-dichloro-6-N-(4'-chlorophenyl)amino-s-triazine,
2,4-dichloro-6-N-(2',5'-dichlorophenyl)amino-s-triazine,
2,4-dichloro-6-N-(4'-methoxyphenyl)amino-s-triazine,
2,4-dichloro-6-N-(3'-sulphophenyl)amino-s-triazine,
2,4-dichloro-6-N-(2',5'-dichloro-4'-sulphophenyl)amino-s-triazine
2,4-dichloro-6-N-(2',5'-disulphophenyl)amino-s-triazine,
2,4-dichloro-6-N-(2'-methylphenyl)amino-s-triazine,
2,4-dichloro-6-N-(2',4'-dimethylphenyl)amino-s-triazine,
2,4-dibromo-6-N-(3'-chloro-4'-methylphenyl)amino-s-triazine,
2,4-dibromo-6-N-(4'-ethoxyphenyl)amino-s-triazine,
2,4-dichloro-6-N-(2'-nitro-4'-methylphenyl)amino-s-triazine,
2,4-dichloro-6-N-(4'-nitrophenyl)amino-s-triazine,
2,4-dichloro-6-N-naphth-1'-yl-amino-s-triazine,
2,4-dichloro-6-N-naphth-2'-yl-amino-s-triazine, 2,4-dichloro-6-N-(1'-sulphonaphth-2'-yl)amino-s-triazine,
2,4-dichloro-6-N-(1'-sulphonaphth-4'-yl)amino-s-triazine,
2,4-dichloro-6-N-(2'-sulphonaphth-5'-yl)amino-s-triazine,
2,4-dichloro-6-N-(1',3'-disulphonaphth-6'-yl)amino-s-triazine,
2,4-dichloro-6-N-(1',3'-disulphonaphth-7'-yl)amino-s-triazine, Compounds of the formula (2) are known. They can be manufactured by condensation of 2,4,6-trihalo-s-triazines with amines, e.g. methylamine, ethylamine, propylamine, aniline, ammonia etc., in aqueous solution and in the presence of an acid acceptor.

The novel process is surprising, since it has so far not proved possible to react the dichloro-amino-s-triazine with one of the conventionally used alkyl- or arylisocyanates. It is also surprising that the N-(2,4-dihalo-s-triazin-6-yl)-ureas of the formula (3), which are highly reactive compounds, can be obtained by hydrolysis and processing in aqueous solution without thereby — as would have been expected — reacting further with the water accompanied by the splitting off of hydrogen chloride. The feasibility and the reaction course of the novel process were therefore not be expected.

Compared with the known process, the novel process affords practical advantages on account of the easier accessibility of the starting materials and because it is easier to carry out. Furthermore, it can also be applied to orther heterocyclic compounds.

The compounds of the formula (3) are characterised by an unexpectedly high reactivity. They can therefore easily by hydrolysed further with one halogen atom of the s-triazine being replaced by a hydroxy group. In particular, they are suitable as starting products for the manufacture of reactive dyes, fluorescent whiteners, or agrochemicals.

The following Examples illustrate the invention, the parts and percentages being by weight unless otherwise stated.

EXAMPLE 1

N-(2,4-dichloro-s-triazin-6-yl)-urea

With stirring, a solution of 75 parts of chlorosulphonylisocyanate in 200 parts by volume of acetonitrile is added dropwise to a solution of 82.5 parts of 2,4-dichloro-6-amino-s-triazine in 200 parts by volume of acetronitrile in such a manner that the temperature of the reaction mixture does not rise above 45°C. Stirring is then continued for 2 hours at this temperature and for 2 hours at room temperature. Then 800 parts by volume of water are added in such manner that the temperature rises initially to 70°–75°C, but is then immediately lowered to about 40°C through the surplus of water. The precipitate that has fallen out is immediately suctioned off, washed twice water, once with phosphate buffer (pH = 7.0) and acetone respectively and dried in vacuo over phosphorus pentoxide, to yield 87.4 parts of a fine, white powder that contains at least 95% of N-(2,4-dichloro-s-triazin-6-yl)-urea as can be shown by comparison with material manufactured in another manner (analysis, IR spectrum, mass spectrum).

Analysis: calculated: $C_4H_3Cl_2N_5O$): 23,10% C; 1,45% H; 33,67% N; 34,09% Cl; found: 22.9% C; 1,7% H; 33,5% N; 33,9% Cl.

EXAMPLE 2

N-(2,4-dichloro-s-triazin-6-yl)-N-methyl-urea

By using 89 parts of 2,4-dichloro-6-methyl-amino-s-triazine instead of 82.5 parts of 2,4-dichloro-6-amino-s-triazine and otherwise carrying out the procedure as described in Example 1 for the manufacture of N-(2,4-dichloro-s-triazin-6-yl)-urea, there are obtained 79.5 parts of N-(2,4-dichloro-s-triazin-6-yl)-N-methyl-urea with a melting point of 172°–174°C.

Analysis: calculated: $(C_5H_5Cl_2N_5O$: 27,05% C; 2,27% H; 31,54%N; 31,93% Cl; found: 27,3% C; 2,4% H; 31,5% N; 31,5% Cl.

EXAMPLE 3

N-(2,4-dichloro-s-triazin-6-yl)-N'-sulpho-urea

A solution of 60 parts of chlorosulphonylisocyanate in 200 parts by volume of dioxan is added dropwise to a solution of 66 parts of 2,4-dichloro-6-amino-s-triazine in 200 parts by volume of dioxan. The mixture is heated for 2 hours to 70°C to 80°C and then cooled to room temperature. The reaction solution is added dropwise to a solution of 2 parts of secondary sodium phosphate in 800 parts by volume of water in such a manner that the temperature does not rise above 20°C. During this addition the pH is kept constant at 8.0 with 200 parts by volume of sodium hydroxide solution which contains 16 parts of NaOH in 100 parts by volume. The resulting solution of the sodium salt of N-(2,4-dichloro-s-triazin-6-yl)-N'-sulpho-urea can be used direct for the acylation of suitable amines.

By reacting one equivalent of the above solution with 2.5 equivalents of metanilic acid, it is still possible to detect 0.55 equivalent of metalinic acid by means of titration after the reaction, which indicates that the reactive portion contains two active chlorine atoms.

Alternatively, by reacting the above solution with 1 equivalent of aniline, a solid of the following composition can be isolated after the reaction by salting out and purifying:

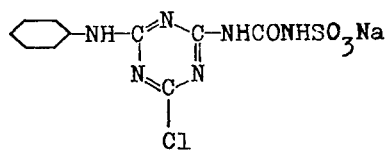

Analysis: calculated:$(C_{10}H_8ClN_6NaO_4S)$: 32,75% C; 9.67% Cl; 22,92% N; 8,74% S; found: 32,0% C; 10,1% Cl; 22,1% N; 8,2% S.

EXAMPLE 4

N-(2,4-dichloro-s-triazin-6-yl)-N-methyl-N'-sulpho-urea

A solution of the sodium salt of N-(2,4-dichloro-s-triazin-6-yl)-N-methyl-N'-sulpho-urea, which can also be used direct for the acylation of suitable amines, is obtained by using 89.5 parts of 2,4-dichloro-6-methyl-amino-s-triazine instead of 82.5 parts of 2,4-dichloro-6-amino-s-triazine and otherwise carrying out exactly the same procedure as in the manufacture of the sodium salt of N-(2,4-dichloro-s-triazin-6-yl)-N'-sulpho-urea.

EXAMPLE 5

N-(2,4-dichloro-s-triazin-6-yl)-N-phenyl-urea

A solution of 30 parts of dichlorosulphonylisocyanate in 100 parts of dry acetronitrile is slowly added dropwise to a suspension of 48.22 parts of 2,4-dichloro-6-phenylamino-s-triazine in 100 parts by volume of dry acetonitrile. The mixture is warmed gently and soon a clear, slightly yellowish solution forms. The reaction is brought to completion by subsequently stirring the solution for about 2 hours at 45°–50°C and then for 2 hours at room temperature. Then 320 parts by volume of water are added in such a manner that the temperature rises initially to 70°–75°C but is then immediately lowered. The precipitate which has formed is filtered off with suction, washed neutral with water and dried in vacuo to yield 52 parts of N-(2,4-dichloro-s-triazin-6-yl)-N-phenyl-urea which melts at 151°–154°C and is pure enough for most reactions. Recrystallisation from perchloroethylene yields a white, crystalline product which melts at 155°–157°C and has the following analytical values:

Calculated: ($C_{10}H_7Cl_2N_5O$): 42,48%C; 2,48%H; 24,65%N; 24,96%Cl; found: 42,8%C; 2,6%H; 24,5%N; 24,5%Cl.

The 2,4-dichloro-6-phenylamino-s-triazine used as starting material can be manufactured from cyanuric chloride and aniline hydrochloride according to the directions of German Auslegeschrift 1 670 675

EXAMPLE 6

N-(2,4-dichloro-s-triazin-6-yl)-N-phenyl-N'-sulpho-urea 120 parts of 2,4-dichloro-6-phenylamino-s-triazine in 200 parts by volume of dioxan are treated slowly with a solution of 75 parts of chlorosulphonylisocyanate in 200 parts by volume of dioxan. After the reaction has been brought to completion by stirring for about 2 hours at 40°–50°C, the resulting solution is poured on 500 parts by volume of water while the pH is kept at 8.0 by simultaneous addition of about 125 parts by volume of 8 normal sodium hydroxide solution, to give a solution of the sodium salt of N-(2,4-dichloro-s-triazin-6-yl)-N-phenyl-N'-sulpho-urea which can be used direct for the acylation of suitable compounds.

In analogous fashion to the preceding Examples, by reacting the 2,4-dichloro-6-amino-s-triazines of column 1 of the Table with chlorosulphonylisocyanate and subsequent acid processing it is possible to obtain the N-(2,4-dichloro-s-triazin-6-yl)-ureas of column 2 and by alkaline processing the salts of the N-(2,4-dichloro-s-triazin-6-yl)-N'-sulpho-ureas of column 3.

Table

| 1 | 2 | 3 |
|---|---|---|
| 2,4-dichloro-6-(ethylamino)-s-triazine | N-(2,4-dichloro-s-triazin-6-yl)-N-ethyl-urea | N-(2,4-dichloro-s-triazin-6-yl)-N-ethyl-N'-sulpho-urea |
| 2,4-dichloro-6-(propylamino)-s-triazine | N-(2,4-dichloro-s-triazin-6-yl)-N-propyl-urea | N-(2,4-dichloro-s-triazin-6-yl)-N-propyl-N'-sulpho-urea |
| 2,4-dichloro-6-(4-chlorophenylamino)-s-triazine | N-(2,4-dichloro-s-triazin-6-yl)-N-(4-chlorophenyl)-urea | N-(2,4-dichloro-s-triazin-6-yl)-N-(4-chlorophenyl)-N'-sulpho-urea |
| 2,4-dichloro-6-(4-nitrophenylamino)-s-triazine | N-(2,4-dichloro-s-triazin-6-yl)-N-(4-nitrophenyl)-urea | N-(2,4-dichloro-s-triazin-6-yl)-N-(4-nitrophenyl)-N'-sulpho-urea |

TABLE — Continued

| 1 | 2 | 3 |
|---|---|---|
| 4,6-dichloro-2-[(2-chlorocyclohexyl)amino]-1,3,5-triazine | 4,6-dichloro-1,3,5-triazin-2-yl(2-chlorocyclohexyl)carbamide | 4,6-dichloro-1,3,5-triazin-2-yl(2-chlorocyclohexyl)sulfamoylcarbamate |
| 4,6-dichloro-2-(propylamino)-1,3,5-triazine (Cl₂-triazine-NHCH₂CH₂CH₃) | Cl₂-triazine-N(CH₂CH₂CH₂CH₃)CONH₂ | Cl₂-triazine-N(CH₂CH₂CH₂CH₃)CONHSO₃H |
| Cl₂-triazine-NH-CH₂CH(CH₃)₂ | Cl₂-triazine-N(CH₂CH(CH₃)₂)CONH₂ | Cl₂-triazine-N(CH₂CH(CH₃)₂)CONHSO₃H |
| Cl₂-triazine-NHCH₂CH₂OCH₂CH₃ | Cl₂-triazine-N(CH₂CH₂OCH₂CH₃)CONH₂ | Cl₂-triazine-N(CH₂CH₂OCH₂CH₃)CONHSO₃H |
| Cl₂-triazine-NH-(4-methoxycyclohexyl) | Cl₂-triazine-N(4-methoxycyclohexyl)CONH₂ | Cl₂-triazine-N(4-methoxycyclohexyl)CONHSO₃H |
| Cl₂-triazine-NH-(4-methylcyclohexyl) | Cl₂-triazine-N(4-methylcyclohexyl)CONH₂ | Cl₂-triazine-N(4-methylcyclohexyl)CONHSO₃H |

Note: This table reproduces structural drawings. Each row shows column 1 as a 2-(alkyl/cycloalkyl-amino)-4,6-dichloro-1,3,5-triazine, column 2 as its N-carbamoyl derivative (—NCONH₂), and column 3 as the corresponding N-(sulfamoylcarbamoyl) derivative (—NCONHSO₃H).

I claim:
1. A process for the manufacture of a N-(2,4-dihalo-s-triazin-6-yl)-urea of the formula

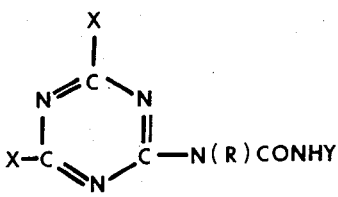

wherein X is halogen, R is lower alkyl, lower alkoxy-lower alkyl, phenyl, halophenyl, nitrophenyl, lower alkyl-phenyl, lower alkoxy-phenyl or hydrogen and Y is hydrogen or the sulphonic acid group, which comprises reacting a dihalo-amino-s-triazine of the formula

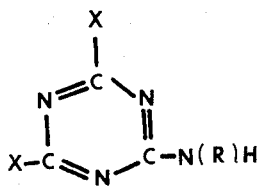

wherein X and R have the meanings assigned to them herein before, with chloro-sulphonylisocyanate and hydrolysing the resulting reaction product.

2. A process according to claim 1 for the manufacture of N-(2,4-dihalo-s-triazin-6-yl)-urea of the formula

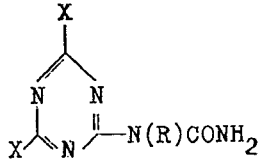

wherein X is chlorine and R is alkyl with 1 to 4 carbon atoms, phenyl or hydrogen, which comprises reacting a compound of the formula (2), wherein X and R have the meanings assigned to them hereinbefore, with chlorosulphonylisocyanate and hydrolysing the resulting reaction product in acid solution.

3. A process according to claim 2 for the manufacture of N-(2,4-dichloro-s-triazin-6-yl)-urea, which comprises reacting 2,4-dichloro-6-amino-s-triazine with chlorosulphonylisocyanate and hydrolysing the resulting reaction product in acid solution.

4. A process according to claim 1 for the manufacture of N-(2,4-dichloro-s-triazin-6-yl)-N'sulpho-urea of the formula

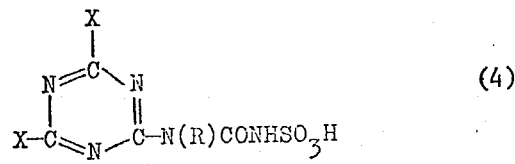

wherein X is chlorine and R is alkyl with 1 to 4 carbon atoms, phenyl or hydrogen, which comprises reacting a dihalo-amino-s-triazine of the formula (2), wherein X and R have the meanings assigned to them hereinbefore, with chlorosulphonylisocyanate and hydrolysing the resulting reaction product in weakly alkaline solution.

5. A process according to claim 4 for the manufacture of N-(2,4-dichloro-s-triazin-6-yl)-N'-sulpho-urea, which comprises reacting 2,4-dichloro-6-amino-s-triazine with chlorosulphonylisocyanate and hydrolysing the reaction product in weakly alkaline solution.

6. A process according to claim 1, which comprises reacting a dihalo-amino-s-triazine of the formula (2), wherein X and R have the meanings assigned to them in claim 1, with chlorosulphonylisocyanate in a water-miscible organic solvent and, by addition of water, hydrolysing the reaction product in the same solution.

7. A N-(2,4-dihalo-s-triazin-6-yl)-urea of the formula

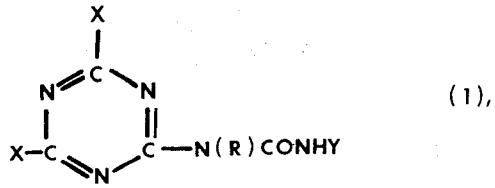

wherein X is halogen, R is lower alkyl, lower alkoxy-lower alkyl, phenyl, halophenyl, nitrophenyl, lower alkyl-phenyl, lower alkoxy-phenyl or hydrogen and Y is the sulphonic acid group.

8. A N-(2,4-dichloro-s-triazin-6-yl)-N'-sulpho-urea according to claim 7, of the formula

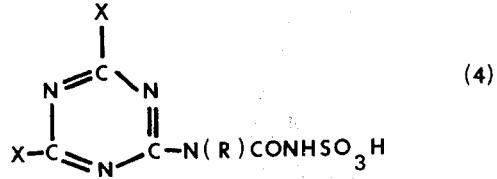

wherein X is chlorine and R is alkyl with 1 to 4 carbon atoms, phenyl or hydrogen.

9. A N-(2,4-dichloro-s-triazin-6-yl)-N'-sulpho-urea according to claim 8.

* * * * *